United States Patent [19]

Knorr et al.

[11] Patent Number: 4,633,083

[45] Date of Patent: Dec. 30, 1986

[54] CHEMICAL ANALYSIS BY TIME DISPERSIVE ION SPECTROMETRY

[75] Inventors: Fritz J. Knorr, Moscow, Id.; Randy L. Eatherton, Pullman, Wash.; William F. Siems, Spokane, Wash.; Herbert H. Hill, Jr., Pullman, Wash.

[73] Assignee: Washington State University Research Foundation, Inc., Wash.

[21] Appl. No.: 724,514

[22] Filed: Apr. 18, 1985

[51] Int. Cl.⁴ .............................................. B01D 59/44
[52] U.S. Cl. ..................................... 250/282; 250/287
[58] Field of Search ................ 250/281, 282, 286, 287

[56] References Cited

U.S. PATENT DOCUMENTS

| | | |
|---|---|---|
| 3,553,452 | 1/1971 | Tierman et al. .................... 250/287 |
| 3,626,180 | 12/1971 | Carroll . |
| 3,629,574 | 12/1971 | Carroll .............................. 250/287 |
| 3,668,383 | 6/1972 | Carroll . |
| 3,668,384 | 6/1972 | Moorman et al. . |
| 3,920,978 | 11/1975 | Schmitt et al. . |
| 3,989,938 | 11/1976 | Auth . |
| 4,390,784 | 6/1983 | Browning et al. ................. 250/286 |

OTHER PUBLICATIONS

Articles: By M. A. Baim and H. H. Hill, Jr., Analytical Chemistry, 1982, vol. 54, p. 33.
Brochures: PCP, Inc. entitled "Ion Molecule Reactor Ion Mobility Spectrometer-Quadrupole Mass Spectrometer".
PCP, Inc. entitled "Phemto-Chem Atmosphere Ion Mobility Spectrometer".
PCP, Inc. "Bibliography of Plasma Chromatography Literature".
PCP, Inc.—"Bibliography Additions Since May, 1979".

Primary Examiner—Bruce C. Anderson
Attorney, Agent, or Firm—Wells, St. John & Roberts

[57] ABSTRACT

Methods and apparatus for time dispersive ion spectroscopy such as ion mobility spectroscopy. The methods include ionizing molecules of a sample and controllably admitting pulses of the resulting ions into a drift region. The drift region has an electric field therein which forces the admitted ions through the drift region. Ions emitted from the drift region during a gate open period simultaneous with the ion admission period are exclusively detected resulting in an ion detection signal. Data is recorded for the frequency rate at which the ion pulses are admitted to the drift region and the associated ion detector signal. The frequency of admitted ion pulses is scanned over a relevant range during which the ion admission period also varies. Data recorded for frequency and ion detection can be recorded and/or transformed such as by a Fourier transform to produce time dispersive spectra in the form of ion intensity or quantity as a function of the time period necessary for the ions to transit the drift region. Such spectra are useful in identifying constituents such as organic compounds contained in the sample. The methods and apparatus allow rapid analysis of samples and can be used to simultaneously analyze discharges from sample separation apparatus such as a capillary gas chromatograph.

20 Claims, 10 Drawing Figures

FIG 8

CHEMICAL ANALYSIS BY TIME DISPERSIVE ION SPECTROMETRY

TECHNICAL FIELD

The technical field of this invention includes methods and apparatus for time dispersive spectrometric analysis for determining the chemical constituents of a sample, such as ion mobility spectrometry.

BACKGROUND

Ion mobility spectrometry is an analytical technique used in chemistry to analyze and detect a wide variety of chemical compounds. Ion mobility spectrometry has been found to be particularly advantageous for detecting trace amounts of organic molecules. Ion mobility spectrometry is also known by the name plasma chromatography.

The first step of ion mobility spectrometry is to take a sample and pass it through an ionizer to produce electrically charged molecules usually called ions. These ions are allowed to enter a drift region provided with an electric field which causes the charged molecules to move through the drift region. An electrical gate is provided to control the entrance of ions at one end of the drift region. An ion detector is provided at or near the opposite end of the drift region to detect ions which have traversed therethrough.

The drift region is provided with a steady flow of relatively inert drift gas flowing opposite to the direction that the ions travel under the force of the electric field. The time which it takes for ions to travel from the entrance gate across the drift region depends upon the mass, geometry and size of the molecule, its electrical charge, and the distance which must be traveled. Other factors may also effect the velocity or mobility of the ions in the drift region to produce varying transit times which are characteristic or indicative of the types of molecules present.

Ion mobility spectrometers can be used as detectors for gas chromatographs or to further analyze the outflow from a gas chromatograph to provide data useful in identifying the constituents of the sample being analyzed. One popular type of gas chromatograph incorporates a long, relatively small diameter capillary tube which is either coated or uncoated. The sample gas is heated and introduced into the capillary tube. The constituents of the sample proceed through the tube swept along by a very small flow of helium or other appropriate carrier gas. Different molecules pass through the capillary tube in differing amounts of time, thus allowing the sample to be segregated into different constituents which exit the capillary over a range of times. The constituents exit the capillary tube and are detected by some form of chromatographic detector.

It has been found that ion mobility spectrometers can advantageously be used as chromatographic detectors to analyze the outflow from a gas chromatograph to provide ultrasensitive detection of organic and other compounds contained therein. Unfortunately, prior methods for using ion mobility spectrometers as detectors for gas chromatographs have not proven satisfactory in many applications and have not gained wide acceptance.

Presently there are three methods used in ion mobility spectrometry. The first is the single scan method which involves opening the entrance gate for a short period of time to admit ions into the drift region. The entrance gate is typically left open for approximately 0.2 millisecond before it is closed thereby blocking further ions from entering the drift region. The pulse of ions admitted during the period the entrance gate is open move down the drift region under the force of the electric field countercurrent to the drift gas. In the single scan method there is no exit gate and the ions strike directly onto the ion detector. The ion detector is connected to an oscilloscope which is used to directly monitor the output of the ion detector. The single scan method suffers from high noise levels in the detector output signal and accordingly cannot be used for high resolution chromatographic separations.

The second method used in ion mobility spectrometry is termed the signal averaging method. The signal averaging method again involves opening the entrance gate to allow a pulse of ions to pass into the drift region and be propelled therethrough under the force of the electric field. The ions again strike directly upon the ion detector, as in the single scan method. In the signal averaging method, many repetitions of single scans are performed and recorded such as with a computer. Five hundred to 1,000 repetitions are often required to provide statistically acceptable signal to noise levels. Such numerous repetitions typically require a minimum of 10 to 20 seconds to perform thereby rendering the method unacceptable for high resolution chromatographic separation of sample constituents on an on-line basis as they flow directly from a capillary or other gas chromatograph.

The third method currently used in ion mobility spectrometry is termed the moving second gate method. Such method is used on ion mobility spectrometers having an exit gate which is located at the end of the drift region prior to the ion detector. A pulse of ions are admitted through the entrance gate and propelled through the drift region under the force of the electric field. The second or exit gate positioned at the end of the drift region selectively opens for a short period of time usually equal to the time the entrance gate is opened. The delay time between opening of the entrance and opening of the exit gate is the control variable which is varied over a range of delay times. The time delay between opening of the entrance gate and subsequent opening of the exit gate thus allows only ions having transit times approximately equal to the delay to pass through the exit gate and onto the ion detector where the strength of the measured signal indicates the quantity of ions having such transit time.

The time delay between the opening of the entrance gate and the opening of the exit gate is varied over a range of relevant transit times and a large number of experimental ion pulses are needed in order to generate acceptable data indicating ion quantity (signal strength) as a function of ion transit time. Because of the large number of different delay times which must be tested, the amount of time necessary to test the full spectrum of transit times with sufficient specificity, accuracy, and to obtain acceptable signal to noise levels thus requires testing for a minimum of one or two minutes. Thus the moving second gate method is also not acceptable for analyzing constituents as they flow directly from a gas chromatograph.

None of the three methods described above make efficient use of the available ions and this is particularly true with the moving second gate method. Typical entrance gate pulse durations of 0.2 milliseconds with recurrent pulses every 20 milliseconds allow only one percent of the available ions from the sample to pass into the drift region. This small proportion of the available ions admitted into the drift region is further reduced in the moving second gate method by the selective opening and closing of the exit gate for approximately similar periods of time. This results in an average of only one percent of the ions admitted through the entrance gate passing through the exit gate and onto the ion detector. The resulting 0.01 percent utilization of available ions allows only a relatively weak signal to be developed at the ion detector, thus causing a poor signal to noise ratio. Opening the entrance and exit gates for longer periods of time increases the signal strength but lowers the resolution of the spectrometer. Resolution is reduced because the available time between opening of the entrance gate and closing of the exit gate is greater and the range of successful transit times also increases. This tends to blur the resulting detector signal and detracts from the acceptability of the method for determining sample constituents.

In any method a short duration pulse of ions entering through the entrance gate provides greater resolution but is relatively weak because of the small number of ions available to strike the detector. The resulting low level ion detector signals cause the signal to noise ratio to become unacceptably high for producing statistically accurate results unless a very large number of ion pulses are tested. Increasing the number of ion pulses tested requires greater amounts of time for performing an accurate analysis of the sample. Such increased analysis time renders the method unacceptable for use as an on-line detector for capillary gas chromatographs and in other types of chromatographs where the chromatographic eluants are admitted from the chromatograph over periods of time usually ranging from 1–5 seconds in duration.

SUMMARY OF THE INVENTION

It is an object of this invention to provide methods for operating time dispersive spectrometers which reduce the amount of time required to generate data used to produce time dispersive spectra useful in analyzing constituents of a sample being tested.

It is another object of the invention to provide methods for time dispersive spectrometry which efficiently use the available ions contained in a sample being tested.

It is a further object of this invention to provide time dispersive spectrometric apparatus which can efficiently and quickly analyze samples to provide time dispersive spectra indicative of the constituents of the sample.

It is a still further object of this invention to provide time dispersive spectrometry methods and apparatus which can be used to analyze effluent from capillary gas chromatographs.

These and other objects and advantages of the present invention are apparent from the description given herein or from practice of the invention and can be advantageously accomplished using the concepts described in the description of the preferred embodiments given herein.

This invention includes both methods and apparatus for improved ion mobility spectrometry, and similar types of time dispersive spectrometry.

Time dispersive spectrometry methods according to this invention involve ionizing molecules of a sample to produce ions. The ions are controllably admitted into a drift region in pulses by opening an entrance gate for variable short periods of time termed gate open or ion admission periods. Ions admitted into the drift region move therethrough forced by an electric field. Only ions which exit from the defined drift region within the gate open periods are detected by an ion detector, or if detected, are subsequently excluded from consideration. Consideration of only those ions exiting the drift region during gate open periods can be accomplished using an exit gate which simultaneously opens and closes with the opening and closing of the entrance gate, thereby allowing ions to be detected which exit during the gate open periods and excluding ions exiting during complementary gate closed periods. Exclusion of such ions can also be accomplished electronically using an electronic exit gate operative upon the ion detector output signal rather than physically intercepting the ions prior to striking the ion detector.

Simultaneous opening and closing of the entrance and exit gates is varied over a range of frequencies. If the admitted ion pulses arrive at the end of the drift region during a gate open period then they are said to be in phase with the gating function. If the admitted ion pulses arrive at the end of the drift region during a gate closed period then they are said to be out of phase with the gating function. The intensity of the ion pulses detected varies as the frequency of the pulses is varied thereby going in and out of phase with the gating function. Typically the ion pulses and resulting ion detector signal output is in phase with the gating function when the frequency of the gating function is an integer multiple of the inverse of the drift time of the ions being sampled. Also typically the ion pulses and resulting ion detection signal are out of phase with the gating function when the frequency of the gating function is an integer multiple of one half times the inverse of the drift time of the ions being sampled.

Simultaneous opening and closing of the entrance and exit gates defined by the gating function is varied over a range of frequencies to produce associated ranges of times for the gate open periods and gate closed periods. Only ions which exit the defined drift region during the gate open periods are considered in the subsequent analysis.

Data is recorded in the form of the ion detector signal strength as a function of the variable gate frequency. For each type of ion there are a series of maxima in ion detector signal strength when the ion pulses are in phase with the gating function. Correspondingly, for each ion there are a series of minima in ion detector signal strength when the ion pulses are out of phase with the gating function. The ion pulses are thus said to interfere or form an interference function with the gating function. Data in the form of ion detector signal strength as a function of frequency can thus be plotted as an interference function or interferogram displaying such maxima and minima.

The interference function contains information of the quantity of ions having various transit times. This information can be mathematically transformed from the frequency domain to the time domain using a suitable mathematical transform such as a Fourier transform. The resulting transformed data can advantageously be displayed as a graphical plot of ion detector intensity as a function of ion transit times and conveniently compared to previously known similar data to identify the sample constituents and the concentration thereof.

Data can alternatively be recorded as ion detector signal strength as a function of gate open and gate closed periods of time and appropriately transformed mathematically to produce data in the form of ion detector intensity as a function of ion transit time or in other desirable forms for identification or other types of analysis.

Apparatus according to this invention comprise means for electrically charging or ionizing molecules contained within a sample to produce ions. A drift region is provided for the ions to transit therethrough under the force of an electric field. An entrance gate is also provided for controllably allowing ions to enter into the drift region. An ion detector is provided to detect ions exiting the drift region. An exit gate or other means is also advantageously provided for selectively excluding ions which do not exit the drift region during gate open periods. In one embodiment the exit gate can advantageously be positioned at the end of the defined drift region to block ions not emitted during gate open periods. In an alternative embodiment, the drift region extends to the surface of the ion detector and the signal resulting from ions exiting the drift region and striking the ion detector is nullified or otherwise eliminated for ions not emitted during the gate open periods. Such nullification can easily be accomplished by multiplying the gating function times the ion detector signal function.

A gate driver is provided for opening and closing the entrance and exit gate. The gate driver is capable of opening and closing the entrance and exit gates over a variety of frequency rates and durations of gate open and gate closed periods.

Apparatus according to this invention can further advantageously include data storage for recording data indicative of the frequency or period of time during which the entrance and exit gates are opened and closed, and further for recording data indicative of the quantity of ions passing through the drift region and striking the ion detector. Apparatus according to this invention can further advantageously comprise computational means for data manipulation and for performing Fourier or other mathematical transformation of data collected in the form of ion detector signal strength versus the frequency of ion pulses, to produce information indicative of ion quantity as a function of ion transit time.

One advantage of this invention is that a much greater percent of the available ions are utilized. Where the entrance and exit gates are operated using square wave frequency scan with equal gate open and gate closed periods, approximately 25 percent of the available ions are detected by the ion detector. This must be compared with the moving second gate method which utilizes approximately 0.01 percent of the available ions. Such increased utilization of available ions increases the signal strength thus enabling more accurate results in reduced amounts of time.

Another advantage of this invention is the reduced amount of time necessary to generate data used to produce the ion mobility spectra or other time dispersive spectra. Times as low as $\frac{1}{2}$-4 seconds have been used to fully sweep the range of applicable frequencies and to collect the necessary data from which to generate time dispersive spectra indicative of the ion intensity as a function of ion transit time. The ability to generate relatively complete time dispersive spectra in such relatively small amounts of time allows this invention to be used on-line to directly and concurrently analyze discharges from capillary gas chromatographs and other sample sources.

Additional benefits and advantages of this invention will be apparent to those of ordinary skill in the art from the description given herein or from practice of the invention.

BRIEF DESCRIPTION OF THE DRAWINGS

A preferred embodiment of the invention is illustrated in the following drawings in which.

DETAILED DESCRIPTION OF THE PREFERRED EMBODIMENTS

In compliance with the constitutional purpose of the Patent Laws "to promote the progress of science and useful arts" (Article 1, Section 8), applicant submits the following disclosure of the invention.

Figures 1, 2:
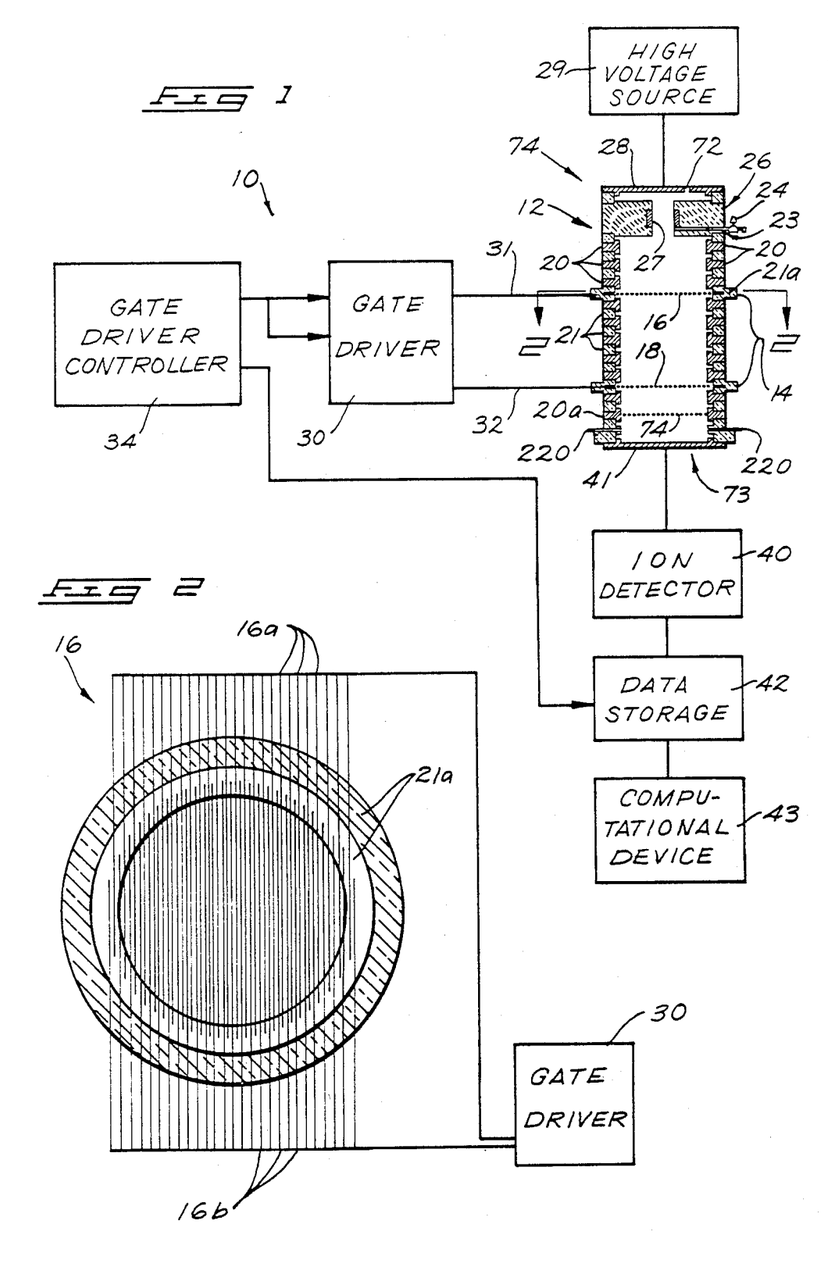
FIG. 1 is a diagrammatic view of an apparatus according to this invention.
FIG. 2 is a diagrammatic cross-sectional view taken along line 2—2 of FIG. 1 showing construction of an entrance gate.

FIG. 1 is a diagrammatic representation of an ion mobility spectrometer 10 constructed in accordance with this invention for performing novel time dispersive spectrometry methods of this invention. Ion mobility spectrometer 10 includes a drift tube assembly 12. Drift tube assembly 12 is advantageously constructed in a generally cylindrical arrangement using a plurality of stainless steel or other conductive electrode rings 20. Electrode rings 20 are electrically insulated from each other using a plurality of interposed insulation rings 21 which are advantageously made of glass. The individual electrode rings 20 are each charged to appropriate electric potentials so as to establish a nearly uniform electric field extending longitudinally down the cylindrical drift tube assembly. Such electric field can easily be accomplished using a high voltage source (not shown) connected to ground through a series of appropriately valued resistors (not shown) with each electrode ring 20 being connected to the successive nodes between such resistors.

Drift tube assembly 12 includes a sample ionizer 26 for ionizing molecules contained in samples being analyzed. Sample ionizer 26 can be of any suitable type. The current preferred sample ionizer uses a circumferential band of nickel isotope 63. Radiation emitted by this radioactive isotope causes the molecules of the sample to be ionized.

A sample port 23 is provided in drift tube assembly 12 through which samples are injected into the drift tube assembly. Sample port 23 can advantageously be provided with a tee fitting 24 so that the incoming sample can be swept along by a carrier gas fed into the other branch of the tee fitting. Typical carrier gases include nitrogen and helium. The incoming sample is released immediately adjacent to sample ionizer 26, preferably upstream thereto in a flow of drift gas proceeding through assembly 12 from bottom to top as shown in FIG. 1.

A plurality of drift gas inlet ports 220 are provided near detector end 73 of drift tube assembly 12. A suitable drift gas such as nitrogen is supplied thereto at pressures slightly greater than atmospheric. The drift gas flows longitudinally through the drift tube in an approximately uniform flow toward sample ionizer 26. Incoming sample molecules are swept from sample inlet port 23 and ionizer 26 where they are ionized. A drift gas exit port 72 is provided at the ionizer end 74 of the drift tube assembly through which the flow of drift gas exits.

Drift tube assembly 12 is further provided with a repeller plate 28 which is electrically connected to a high voltage source 29. Repeller plate 28 repels ions from ionizer 26 and partially down the drift tube assembly countercurrent to the flow of drift gas and into the electric field produced by electrode rings 20.

An entrance gate 16 is also included in drift tube assembly 12 at a point upstream from ionizer 26. FIG. 2 is a schematic sectional view of entrance gate 16. Entrance gate 16 includes an insulative ring 21a which in part serves to insulate the adjacent electrode rings 20. Insulative ring 21a also serves to support a set of first gate electrodes 16a and interposed noncontacting set of second gate electrodes 16b. Electrodes 16a are provided with a common electrode potential, as are electrodes 16b.

When entrance gate 16 is opened for ion movement therethrough both electrode sets 16a and 16b are charged to an electric potential which is intermediate to the potentials of the adjacent electrode rings 20 thereby maintaining continuity in the electric field. When the gate is closed, the first set of electrodes 16a are charged to a gate closed electric potential which differs from the gate open potential by a positive potential differential, for example plus 30 to 45 volts. The second set of electrodes 16b are charged to a gate closed electric potential which is similarly different from the normal or gate open operating potential by a potential differential, such as minus 30 to 45 volts. The dissimilar potentials existing on the closely spaced interposed electrodes 16a and 16b causes a series of transverse electric fields to be established which are sufficiently strong to prevent most ions from passing through entrance gate 16 and traveling down the drift tube.

Drift tube assembly 12 also includes an exit gate 18 similar in construction and operation to entrance gate 16. Exit gate 18 is operated at a normal or open electric potential which is consistent with the potential needed to maintain a continuous electric field. Similar potential differentials are used to close exit gate 18.

A passive gate 74 may be advantageously provided between exit gate 18 and detector plate 41 and maintained at the appropriate potential for the uniform electric field. Passive gate 74 prevents transient noise generated during opening and closing of exit gate 18 from reaching detector plate 41 and causing erroneous signals to be generated thereon.

In the embodiment shown in FIG. 1, there is a drift region 14 defined between entrance gate 16 and exit gate 18. The drift region is the region through which the ions pass to define a transit time. Alternative drift regions are possible such as explained below in another alternative embodiment.

An ion detector 40 having a detector plate 41 is mounted at the end of drift tube assembly 12 in order to receive and detect ions which pass from drift region 14 through exit gate 18. Detector plate 41 is simply a planar appropriately shaped plate made of conductive material such as stainless steel. The detector plate is positioned so that ions emitted from drift region 14 strike the plate thereby causing a change in the electrical charge existing upon the plate.

Ion detector 40 further includes an appropriate electronic device for measuring the change in charge or current caused by impacting ions. This current flow is measured and the charge on the detector plate is neutralized by ion detector 40. Ion detector can advantageously be a very sensitive ammeter operating in the picoampere range. Such an ammeter is specified in Example 1 below, others will clearly be possible. Ion detector 40 can advantageously be set with a variety of response bandwidths depending upon the specific electronic configuration being used.

The drift tube assembly 12 just described and other acceptable components for ion mobility spectrometer 10 may be learned from a description given in an article authored by Michael A. Baim (erroneously printed "Balm") and Herbert H. Hill, Jr., published in Volume 54 of ANALYTICAL CHEMISTRY at pp. 38–43, January 1982 which is hereby incorporated into this specification by reference.

Ion mobility spectrometer 10 further includes a gate driver 30. Gate driver 30 is an electronic apparatus for opening and closing entrance and exit gates 16 and 18. Gate driver 30 is preferably provided with independent channels for independently operating entrance gate 16 and exit gate 18 since the normal operating potential at each gate is different in order to maintain the uniform electric field within drift tube assembly 12. Each channel is constructed so that the first and second sets of electrodes 16a and 16b, respectively, can be charged to electric potential values which are preferably a set number of volts above, for one set, and below, for the other set, when compared to the normal operating potential dictated by the electric field maintained in drift tube assembly 12. Gate driver 30 is preferably capable of responding very quickly to commands that gates 16 and 18 be opened or closed.

A suitable gate driver is described for use in the doctoral thesis of Michael A. Baim, entitled "An Ion Mobility Detector for Gas Chromatography", 1984, available at the Washington State University Engineering and Science Library under call number WSUC51984BC, or available by copy from University Microfilm International, Dissertation Copies, P.O. Box 1764, Ann Arbor, Mich. 48106, Order No. DA8413864. Other alternative high speed, switched, multichannel, high voltage power supplies can clearly be manufactured by those skilled in the art of electronic power supply.

Ion mobility spectrometer 10 further includes a gate driver controller 34 for controlling gate driver 30 so as to switch gates 16 and 18 between open and closed. Gate driver controller 34 can advantageously be a variable frequency square or other waveform generator provided with the capability to linearly scan the frequency of the square wave or other periodic output signal. The scanning capability is desired so that the frequency of the gate driver controller output signal can be varied over a relevant range of frequencies in order to easily perform the methods of this invention. Such scanning waveform generators and other alternative gate driving controllers are known in the art of electronic control systems. An acceptable apparatus is specified in Example 3. Alternative means may be available or hereafter developed which can function as a gate driver controller 34 or which may combine the functions of gate driver controller 34 and gate driver 30 into a single gate driver to control the entrance and exit gate operation over a range of suitable waveform or other periodic frequencies for constructing the apparatus and performing the methods of this invention.

Ion mobility spectrometer 10 is preferably provided with a data storage device 42 which is connected to ion detector 40 and to gate driver controller 34. Data storage device 42 preferably includes a fast analog to digital conversion feature which takes the analog output signal from ion detector 40 and encodes it into digital format. The information is then stored in any suitable type of electronically accessed memory device, well known in the art. Data storage device 42 is preferably provided with input from gate driver controller 34 indicating the applicable frequency at which the entrance and exit gates are being opened and closed. This data is also stored and associated with the corresponding ion detector data. Storage of frequency data is particularly important when fast scanning of gate frequencies occurs. Frequency data transmission can be accomplished using a short duration trigger pulse generated by the gate driver controller at the start of each frequency sweep with the frequency determined for any particular point by such trigger pulse and the frequency scan rate of controller 34. Alternatively, frequency can be scanned stepwise. In such a case a short trigger pulse can be generated at each successive frequency and sent to data storage 42 to signal the shift to the next successive storage register. The ion detector output signals associated with the particular frequency at which the entrance and exit gates are being simultaneously driven, is correlated and subsequently used to generate an interferogram plotting ion detector current as a function of frequency, such as that illustrated in FIG. 5.

Spectrometer 10 further advantageously includes a computational device 43 which is either integrated with or connected to data storage 42. The preferred embodiment incorporates both data storage 42 and computational device 43 into a single digital computer such as an Apple IIe computer from Apple Computer, Inc., Cupertino, Calif. Computational device 43 is used for transforming data in the form of ion detector current as a function of frequency. Such data is preferably transformed using an appropriate Fourier transform, widely available as computer software packages such as explained in the Examples given below. Such transformation results in data in the form of ion current or intensity as a function of transit time. This form of data is the form currently used by scientists in interpreting and correlating data from ion mobility spectrometers and similar time dispersive spectrometers.

The features and principles described above with regard to ion mobility spectrometer 10 can be applied to produce an instrument useful for chemical analysis using the methods which will now be described.

Methods according to this invention apply generally to time dispersive spectrometric analysis. Application of the invention to methods for conducting ion mobility spectrometry using ion mobility spectrometer 10 will be described in detail. Expansion and application of these methods and concepts will become obvious to one of ordinary skill in the art from the description given herein.

Methods according to this invention include the step of ionizing molecules of a sample to produce ions. Ionization of the sample molecules can be accomplished as described above or can be done according to other ionization techniques known or hereafter developed. The electrically charged ions are controllably admitted into a drift region such as drift region 14, for the purpose of measuring the various times required for the ions to transit the drift region. The ions are admitted in brief pulses during periods alternatively referred to as ion admission periods or gate open periods which vary in duration.

The admitted ions are forced through the drift region using an electric field such as the field produced by electrode rings 20. The ions traverse the drift region countercurrent to a flow of drift gas.

The drift region through which the ions traverse is defined for easy and reliable measurement of the transit times of the ions traveling therethrough. Admission of the ions into the drift region can be well defined by an entrance gate, such as entrance gate 16. The opposite end of the drift region can advantageously be defined by an exit gate such as exit gate 18, or alternatively, be defined by the surface of detector plate 41. The end of the allowable period for passage of ions through the exit gate and from the drift region can be defined accurately by closing the exit gate. Alternatively, exit of ions from a drift region defined to extend to the surface of detector plate 41 can easily be recorded by the resulting instantaneous charge on or impinging upon current detector plate 41 and the signal generated by detector 40 as a result thereof. Accurate control of the exit gate or detection of the ions is needed to produce accurate data of ion transit times.

Methods according to this invention require that the quantity of ions emitted from the drift region be measured or considered only during the gate open periods. The gate open periods are the same for entrance and exit gates. These gate open or ion admission periods are conveniently made concurrent by simultaneously opening and closing both the entrance and exit gate. Ions which exit the drift region during a gate open period need not necessarily transit the entire drift region during that single period. Ions may take multiple gate open periods and complementary gate closed periods to fully transit the drift region. It is, however, necessary that ions which reach the drift region boundary during gate closed periods not be considered.

In an alternative method according to this invention, no exit gate is provided. Instead, ions are all allowed to transit the drift region which is defined to end at the detector plate. Ions which are not emitted from the drift region during the gate open periods are excluded from consideration by some appropriate technique. Suitable techniques include nullifying or gating the detector output signal electronically such as by multiplication with the gating function which is defined as equal to one during gate open periods, and equal to zero during gate closed periods. Alternatively, gating can be accomplished by recording data for the appropriate gate open and closed periods and subsequently subtracting the ion signal occurring during gate closed periods by data manipulation.

In either method, ions emitting from the drift region are detected by some suitable form of ion detector such as ion detector 40 and its associated detector plate 41. The ion detector produces an output signal, usually in the picoampere range, which is directly related to the quantity of charge carrying ions which strike the detector plate.

Methods of this invention further include varying the frequency at which the ion admission periods and associated ion pulses occur. The frequency at which the ions pulses are admitted and the duration of the gate open periods determine the possible transit times which ions must have in order to be emitted from the drift region during a gate open period.

Figure 4:
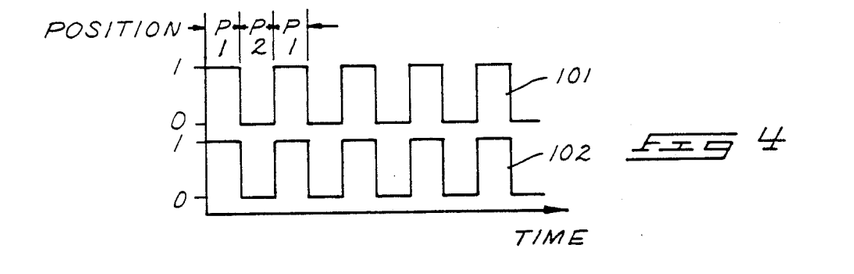
FIG. 4 is a graph illustrating the opening and closing of entrance and exit gates using a method according to the present invention.

FIG. 4 shows schematically the relationship between the operation of an entrance gate and exit gate according to a preferred method of this invention. FIG. 4 shows curves or gating functions 101 and 102 each ranging between 0 and 1 with the passage of time. The 0 level indicates the gate is closed, the 1 level indicates the gate is open. Curve 101 represents the operation of an entrance gate such as 16, and curve 102 represents the operation of an exit gate such as 18. Curves 101 and 102 are simultaneous in time with each gate opening and closing together. Each gate is open for periods P1 defined as the gate open periods or ion admission periods. Each gate is closed a period P2 equal to the gate closed period and period during which ions are not admitted into or emitted from the drift region. The period equal to P1 plus P2 is defined as a gate cycle having a gate cycle period.

FIG. 4 does not show that the frequency of the gate periods is changed with time over a relevant range of frequencies. FIG. 4 indicates that the gate open periods may approximately equal the adjacent gate closed periods in duration, although this does not appear to be necessary for proper performance of the methods of this invention. P1 can be less than, equal to, or even greater than P2. The amount by which P2 can differ from P1 appears limited before loss of intensity will occur. Adjustments in the Fourier transformation may be necessary for transforming data generated when P1 and P2 are not equal.

The applied gate functions 101 and 102 need not necessarily be square wave. Alternative gating functions such as sine wave, triangle wave and others are also theoretically possible although actual operation of the entrance and exit gates in partially open and closed conditions may create unnecessary complexity and signal attenuation. Such alternative gating functions may be found to have specific advantages not presently recognized.

Figure 5:
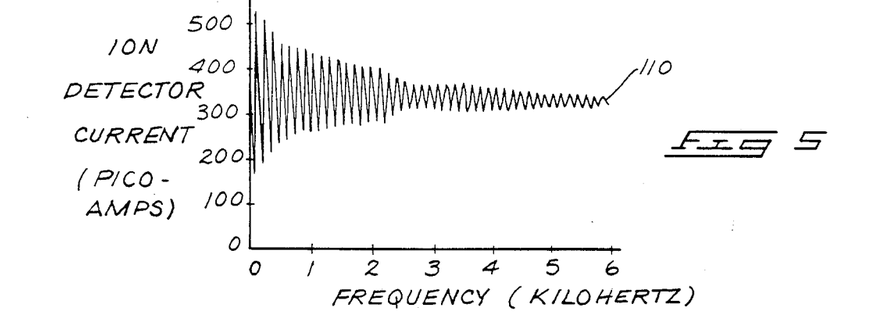
FIG. 5 is a graph showing an example interferogram derived from data produced using a method and apparatus of this invention.
Figure 9:
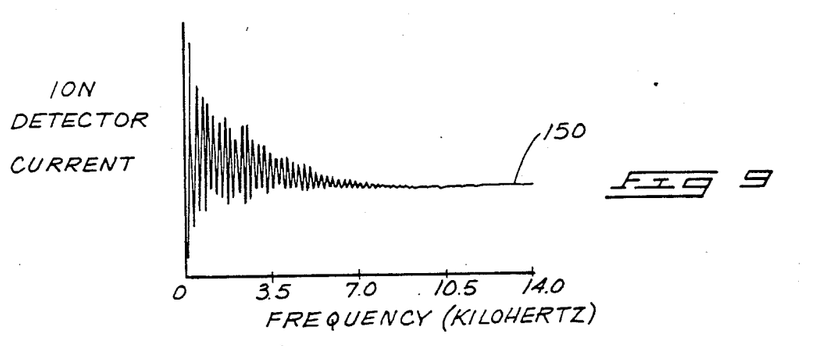
FIG. 9 is a graph showing an interferogram of a sample containing naphthalene generated using a method and apparatus of this invention.

Frequencies over which the ion pulses are admitted typically range between 10 and 20,000 Hertz although higher and lower frequencies are clearly possible. FIGS. 5 and 9 show two example interferograms generated by plotting the ion detector current against the frequency at which the ion pulses were admitted. The curves shown in FIGS. 5 and 9 show periodic highs and lows which can be understood by the fact that at certain frequencies the opening of the entrance gate and closing of the exit gate are not synchronized or in phase with the transit times of the ions, hence causing most ions to be blocked by the exit gate. At other frequencies, the gate open periods and ion velocities are more nearly synchronized or in phase, thereby allowing most of the ions to be successfully emitted from the drift region during a gate open period thus causing high ion detector current.

Methods according to this invention can further advantageously include recording data generated by the ion detector and the gate driver controller or other reliable indicator of frequency. This data can be stored in data storage such as 42 and be subsequently transformed using a Fourier or other mathematical transform to produce data in the form of ion current or intensity as a function of transit time. Use of Fourier transforms are well known in the art such as in the book by R. N. Bracewell, entitled "The Fourier Transform and Its Applications", 2nd edition, McGraw Hill: New York, 1978, which is hereby incorporated by reference hereinto.

EXAMPLE 1

An ion mobility spectrometer was constructed as described in two previously published technical journal articles: the first article is by M. A. Baim and H. H. Hill, Jr., ANALYTICAL CHEMISTRY, 1982, Vol. 54, p. 33. The second article is by M. A. Baim, R. L. Eatherton, H. H. Hill, Jr., ANALYTICAL CHEMISTRY, 1983, Vol. 55, p. 1761. Both such articles are hereby incorporated into this specification by reference.

The drift tube assembly used in this experiment was substantially the same as drift tube assembly 12 described above with regard to the current invention. The entrance and exit gates were independently controlled using an AIM 65 microcomputer manufactured by Rockwell International, Anaheim, Calif. This microcomputer also served as the gate driver controller.

Figure 3:
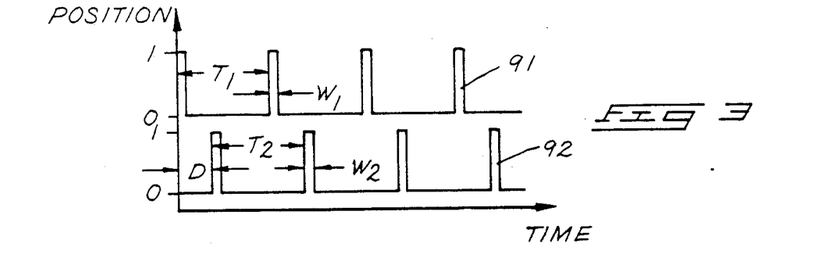
FIG. 3 is a graph illustrating the opening and closing of entrance and exit gates using the prior art moving gate second method for ion mobility spectrometry.

The gate driver controller was programmed to provide entrance and exit gate operation in accordance with the moving second gate method described above in the Background of the Invention and which will be further explained in this Example. FIG. 3 shows two functions 91 and 92 displayed on a graph. The x-axis indicates time from an arbitrary point. The y-axis is subdivided into two scales each marked 0-1. One scale is relevant to function 91 and the other to function 92.

Function 91 indicates the operation of the entrance gate in time with 0 being closed and 1 being open. Function 92 indicates the operation of the exit gate with 0 also being closed and 1 also being open.

The gate driver used to open and close the entrance and exit gates is as described above for gate driver 30.

The entrance gate was opened repeatedly for periods W1 equal to 0.15 millisecond in duration. Similarly the exit gate was opened repeatedly for periods W2 equal to 0.15 millisecond in duration. The time interval between consecutive openings of the entrance gate are indicated by T1 and between consecutive openings of the exit gate are indicated by T2 both of which were equal to 20 milliseconds in duration. The delay time between opening of the entrance gate and opening of the exit gate is designated by D. The moving second gate method varies the delay time D to determine the ion quantities or intensities for a range of various transit times. Characteristic ion transit times from prior experimentation or theoretical development allow the sample constituents to be determined and quantitized.

The ion detector used in this example included a detector plate made of stainless steel sized to cover the detector end of the drift tube. The detector plate was electrically connected to a Keithley 417 high speed picoameter, Keithley Instruments, Cleveland, Ohio. The damping control of the picoameter was set to give a bandwidth of 7 Hz.

The output signal data from the ion detector was collected upon an Apple IIe microcomputer equipped with an Applescope data collection system manufactured by R. C. Electronics, Santa Barbara, Calif.

Other system parameters were as shown below in Table I.

TABLE I

| Ion drift region length: | 7.50 cm |
|---|---|
| Electric field strength: | 239 V/cm |
| Gate closing voltage differentials: | ±30 V |
| Temperature of drift tube: | 150° C. |
| Pressure in drift region: | 691.2 torr |
| Drift gas and sample carrier gas: | Nitrogen |
| Drift gas flow rate: | 600 ml/min |
| Sample carrier gas flow rate: | 20 ml/min |

The experimental procedure first involved testing the drift gas for the background ions formed by the nickel-63 ionization source. This was accomplished by setting the appropriate parameters indicated above and then performing the moving second gate method to generate the ion mobility data. The delay time D ranged from 0.2 milliseconds to 19.8 milliseconds at 0.05 millisecond intervals. Data for the ion detector current was averaged with numerous repetitions at each delay time value in order to overcome the relatively low signal to noise ratio.

Figure 7:
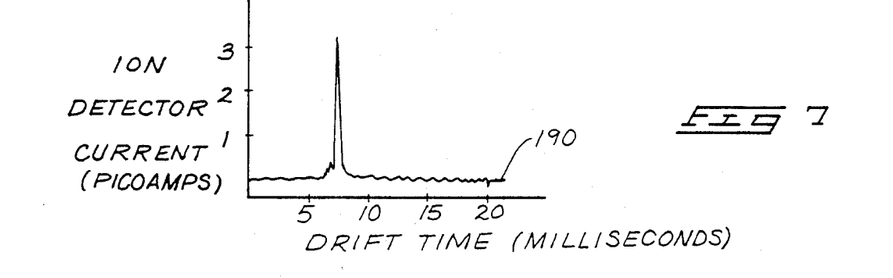
FIG. 7 is a graph showing an ion mobility spectrum obtained using the prior art moving second gate method.

The results obtained are shown in FIG. 7 as curve 190 plotting ion detector current versus the transit time of the ions. FIG. 7 indicates that positively charged background reactant ions are produced which have a transit time between the entrance and exit gate of approximately 7 milliseconds. Such background ions form a baseline spectrum against which subsequent test spectra must be compared to identify ions contained in any samples being analyzed.

The scanning of relevant transit times using the moving second gate method required approximately 54 seconds to generate the necessary data. This amount of time rendered this ion mobility spectrometer unusable for performing on-line analysis of discharges from capillary gas chromatographs because many relevant chromatographic discharges typically occur in periods of a few seconds or less. Concentrations of sample constituents contained in each gas chromatograph discharge may also vary during the period of the discharge, further emphasizing the need for fast analysis.

EXAMPLE 2

The conditions in this Example are the same as those given above in Example 1 except that a sample containing approximately 1 part per million 1-methylnaphthalene in nitrogen gas was injected into the ion mobility spectrometer for testing. Injection was accomplished by placing the sample n a stainless steel sample holder and attaching it to a tee fitting mounted within the oven of a gas chromatograph. The tee fitting was also connected to a flow of nitrogen carrier gas which swept the sample and conveyed it through a connection line to the sample port of the drift tube assembly.

A graphical spectrum of this experiment is not available. The time necessary to perform the moving second gate method required approximately 1 minute.

EXAMPLE 3

An ion mobility spectrometer 10 according to this invention as described above was constructed using an HP3325A synthesizer/function generator manufactured by Hewlett-Packard, Palo Alto, Calif., as the gate driver controller 34. The synthesizer/function generator was operated in a square wave mode at an output voltage of 5 volts peak to peak with a positive offset of 2.5 volts to create proper voltage ranges from the logic circuits of the gate driver. The output of the gate driver controller was connected to two channels of a gate driver 30 constructed as described above and in the thesis of Michael Baim incorporated by reference above. Simultaneous operation of the entrance and exit gates was assured by using the same gate driver controller signal to switch both entrance and exit gate channels of gate driver 30.

The ion detector and data storage devices used were as described in Example 1. Data storage and Fourier transformation were accomplished on an Apple IIe computer using an Applescope data collection system and an SDL-001 Spectrum Analysis Software Option, respectively, both by R. C. Electronics, Santa Barbara, Calif. Data was collected at 1024 different points, recording ion detector current for each such point.

The first experimental procedure required testing the nitrogen drift and sample carrier gases to determine the positive background reactant ions produced by the sample ionizer 26. The gate driver controller, gate driver and entrance and exit gates were initially operated at a frequency of 10 Hz using a waveform as shown in FIG. 4 with P1 equal to P2. The gate driver controller was set to automatically scan linearly from 10 Hz to 6000 Hz over a period of time equal to 36 seconds.

The data recorded by the Apple IIe serving as data storage 42 was in the form of ion detector current as a function of the gate frequency. FIG. 5 is a graph of an interferogram curve 110 which represents the values of ion detector current found for 1024 data points over the range of frequencies scanned.

Figure 6:
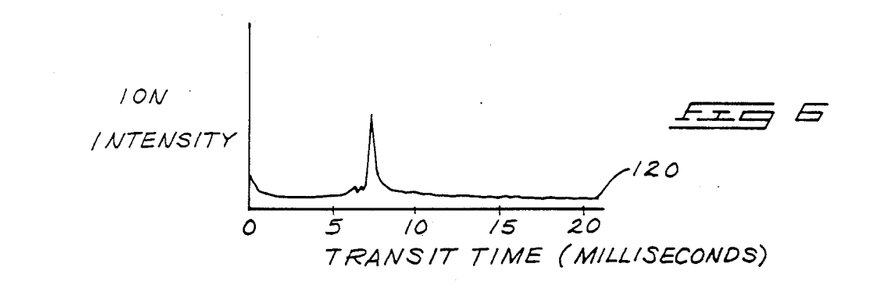
FIG. 6 is a graph showing an ion mobility spectrum derived from the interferogram illustrated in FIG. 5 using a Fourier transformation.

The data used to generate the interferogram of FIG. 5 was transformed using the computer and software package described above in Example 1 to produce a Fourier transform ion mobility spectrum curve 120 shown in FIG. 6. Curve 120 is plotted in the form of ion intensity as a function of transit time, the usual form of ion mobility data. Ion intensity is not scaled but represents the ion detector current. The resulting spectrum indicates that background reactant ions having transit times of approximately 7 milliseconds are the predominant ions produced from the nitrogen drift and sample gases used. Other parameters of this Example are as shown in Table 1.

EXAMPLE 4

The ion mobility spectrometer described above in Example 3 was used to analyze the 1 ppm 1-methylnaphthalene sample described in Example 2 with the sample fed in a similar manner using the same apparatus and the same system parameters shown in Table 1.

Figure 8:
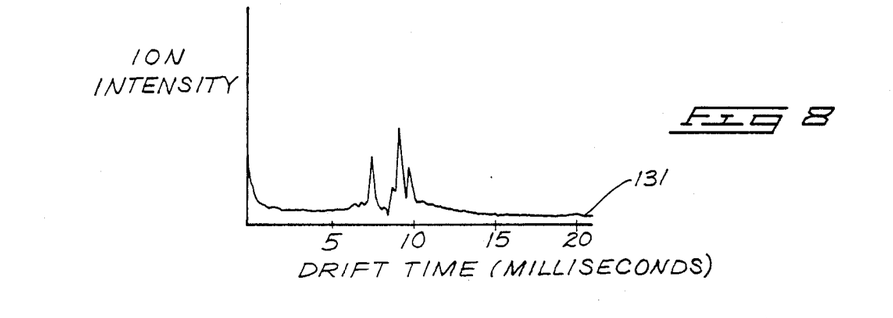
FIG. 8 is a graph showing an ion mobility spectrum of a sample containing approximately 1 part per million 1-methylnaphthalene using the method and apparatus of the present invention.

Data again was collected in the form of ion detector current as a function of the scanned gate frequency. The graphical representation (interferogram) of this data is not available and not shown herein. Such data was transformed using the Fourier transform software described in Example 3 to produce data in the form of ion intensity as a function of transit time. This data is shown in FIG. 8 as Fourier transform ion mobility spectrum curve 131. Study of curve 131 indicates that three definite peaks are present at approximately 7, 8.5 and 9.5 millisecond drift times.

EXAMPLE 5

An ion mobility spectrometer 10 as described above in Example 3 was used to determine minimum frequency scan times necessary to obtain accurate data on the background reactant ions produced during operation of the spectrometer. The gate driver controller described above was replaced by an alternative scanning square wave generator incorporating a 14 bit digital-to-analog converter (Model DAC-HR14B, manufactured by Datel, Mansfield, Mass.) to generate an analog linear voltage ramp. The linear voltage ramp so generated is input to a voltage-to-frequency converter (Model VFC62, manufactured by Burr-Brown, Tucson, Ariz.). The square wave output from such voltage-to-frequency converter can be scanned from 20–20,000 Hz in scan times as low as 0.1 sec and greater, at 0.1 second intervals.

Experimental data was recorded for either 1024 points on the Apple IIe system described in Example 3, or alternatively, for 2048 points when data was recorded on a Data 6000 computer (Data Precision, Danover, Mass.), equipped with appropriate software.

System operating parameters and specifications are as shown below in Table II.

TABLE II

| Ion drift region length: | 7.2 cm |
| Electric field strength: | 333 V/cm |
| Gate closing voltage differentials: | ±41 volts |
| Temperature of drift tube: | 200° C. |
| Pressure in drift region: | 695 torr |
| Nitrogen drift gas flow rate: | 900 mL/min |
| Frequency scan range: | 20–14,020 Hz |

Scan times ranged between 16 seconds to as low as 0.5 seconds. The data generated was used to generate Fourier transform ion mobility spectra (not shown) which were found sufficiently accurate for identifying the background reactant ions.

EXAMPLE 6

The ion mobility spectrometer described in Example 5 was used in conjunction with a Tracor 560 capillary gas chromatograph (Tracor Instruments, Austin, Tex.). One (1) microliter samples containing a test mix of naphthalene; 2,4-dimethylanaline; 2,6-dimethylphenol; and 1-octanol all at sample concentrations of 10 nanograms per microliter.

Operating conditions and parameters were as set out in Table II above. Scan time was set at 4.0 seconds.

Chromatograph operating conditions were as follows:

TABLE III

| Column: | 30 meter × 0.25 mm i.d. fused silica with DB-5 coating |
| Pressure of Helium fed to column: | 15 psig |
| Split ratio: | 40:1 |
| Injection port temperature: | 200° C. |
| Oven temperature: | 100° C. isothermal |
| Transfer line temperature: | 120° C. |

The test mixture specified above was separated in the gas chromatograph providing 4 separate chromatograph discharges. Ion mobility spectroscopy was performed for each discharge during a single gas chromatograph run. FIG. 9 shows an interferogram 150 generated as the naphthalene component passed from the gas chromatograph and was delivered to the sample port of the drift tube assembly using a minute flow of helium carrier gas necessary for operation of the capillary gas chromatograph.

The ion mobility spectrometer was operated by first placing in a standby mode at 20 Hz. Visual observation of a simultaneous graphical printout allowed the gas chromatograph discharges to be monitored. When the ion detector output increased, the operator initiated the gate driver controller to start the preset frequency scan. Scans of 4.0 seconds duration were performed and the data recorded in the Data 6000 computer described in Example 5 using 1024 data points.

Figure 10:
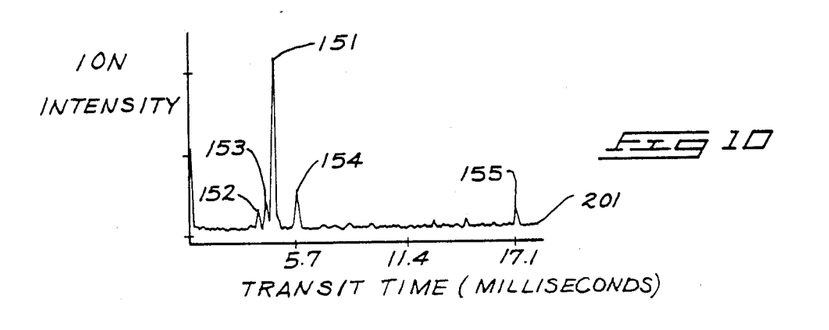
FIG. 10 is a graph showing an ion mobility spectrum transformed from the data shown in the graph of FIG. 9.

Interferogram 150 generated during emission of naphthalene from the gas chromatograph is shown in FIG. 9. The Fourier transformation of this data is shown as spectrum 201 in FIG. 10. Peak 151 is indicative of the mobility and concentration of naphthalene present in the sample. Peaks 152–154 are indicative of background reactant ions. Peak 155 indicates 60 Hz noise in the system.

In compliance with the statute, the invention has been described in language more or less specific as to structural and methodological features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A method for producing data useful in analyzing a sample to identify constituent molecules contained therein; comprising:
   ionizing molecules of the sample to produce ions;
   controllably admitting pulses of said ions into a drift region during gate open periods which reoccur at a variable frequency;
   forcing admitted ions through the drift region by applying an electric field thereto;
   detecting ions which exit from the drift region during said gate open periods;
   varying the duration of said gate open periods and said frequency at which ion pulses are admitted, over relevant ranges of times and frequencies, respectively;
   recording data indicative of a quantity of ions detected exiting the drift region during said gate open periods.

2. The method of claim 1 further comprising:
   recording data indicative of the duration of the gate open periods and said frequency;

transforming said data into at least one time dispersive spectrum indicative of the quantity of ions having various transit times across the drift region for the sample being analyzed.

3. The method of claim 2 further comprising:
comparatively analyzing said time dispersive spectrum against other experimental or theoretical time dispersive data for determining the constituents of said sample.

4. The method of claim 1 wherein said gate open periods are approximately equal in duration to complementary gate closed periods.

5. The method of claim 1 wherein said pulses of ions are admitted using a variable square wave frequency having gate open periods defined thereby which are approximately equal to a consecutive gate closed period during which ions are not admitted into the drift region.

6. The method of claim 5 further comprising:
transforming said data into at least one time dispersive spectrum indicative of the quantity of ions having various transit times across the drift region for the sample being analyzed.

7. The method of claim 6 further comprising:
comparatively analyzing said time dispersive spectrum against other time dispersive data for determining the constituents of said sample.

8. A method for performing time dispersive ion spectroscopy, comprising:
ionizing molecules of a sample to produce ions;
controllably admitting pulses of said ions into a drift region during gate open periods which reoccur at a variable gate frequency;
forcing admitted ions through the drift region by applying an electric field thereto;
controllably emitting ions from the drift region during said gate open periods;
detecting ions which are emitted from the drift region during said gate open periods;
varying the duration of said gate open periods and said gate frequency over relevant ranges of time and frequency, respectively.

9. The method of claim 8 further comprising:
recording data indicative of: quantity of ions detected as emitted from the drift region; durations of said gate open periods; and said gate frequencies at which ion pulses were admitted.

10. The method of claim 9 further comprising:
transforming said data into at least one time dispersive spectrum indicative of the quantity of ions emitted from the drift region as a function of ion transit time through the drift region.

11. The method of claim 10 wherein said transforming is accomplished using a Fourier transformation.

12. The method of claim 8 wherein the gate open periods are approximately equal in duration to gate closed periods during which ions are neither admitted to the drift region nor emitted from the drift region.

13. The method of claim 8 wherein the gate open periods are shorter in duration than gate closed periods during which ions are neither admitted to the drift region nor emitted from the drift regions.

14. The method of claim 8 wherein the gate open periods are longer in duration than gate closed periods during which ions are neither admitted to the drift region nor emitted from the drift region.

15. The method of claim 8 wherein the gate open periods are defined as having duration equal to approximately one half of an associated gate cycle period, and wherein said gate frequency is scanned through the range of relevant frequencies.

16. An apparatus for performing time dispersive spectrometry of a sample, comprising:
means for ionizing molecules of the sample to produce ions;
a drift region; P1 means for creating an electric field within said drift region;
entrance gate means for admitting ions into the drift region;
exit gate means for selectively allowing ions transiting the drift region to be emitted therefrom;
ion detector means for detecting ions emitted from the drift region; and
gate driving means connected to said entrance gate means and said exit gate means for simultaneously opening and closing said entrance gate means and exit gate means; said gate driving means having various frequency rates for simultaneously opening and closing the entrance and exit gate means at various frequencies and durations.

17. The appratus of claim 16 further comprising data storage means for recording data indicative of frequencies at which the entrance and exit gate means are opened, and for recording data indicative of the quantity of ions detected by the ion detector means.

18. The apparatus of claim 17 further comprising computational means for performing transformation of data in the form of quantity of ions detected versus frequency, to produce transformed data in the form of quantity of ions detected as a function of ion transit times across the drift region.

19. An apparatus for performing time dispersive spectroscopy of a sample, comprising:
means for ionizing molecules of the sample to produce ions;
a drift region;
means for creating an electric field within said drift region;
entrance gate means for selectively admitting ions into the drift region;
ion detector means for detecting ions emitted from the drift region and producing a detector signal representative thereof;
gate driving means for opening and closing said entrance gate means; said gate driving means having various frequency rates and durations; and
means for nullifying portions of said detector signal which are associated with ions emitted from the drift region during periods when said entrance gate is closed.

20. The apparatus of claim 19 wherein said means for nullifying comprises computer software used to multiply the detector signal by zero for periods when said entrance gate is closed.

* * * * *